Figure 1:
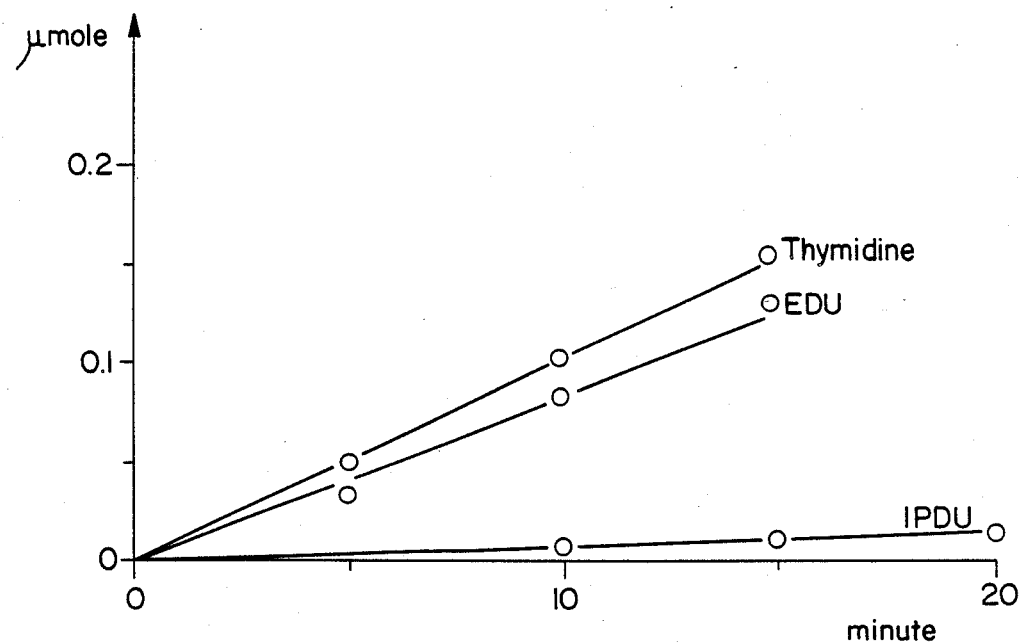

United States Patent [19]

Szabolcs, née, Borbás et al.

[11] Patent Number: 4,937,233
[45] Date of Patent: Jun. 26, 1990

[54] METHOD OF TREATING HERPES EYE INFECTIONS WITH 5-PROPYL-2'DEOXYURIDINE

[75] Inventors: Anna Szabolcs, née, Borbás; László Ötvös; János Sági; Helga Tudös, née Feuer; Attila Szemzö; Zsuzsa Veres; István Szinai; Miklós Vajda, all of Budapest; István Csernus, Debrecen; Katalin Marossy, Debrecen; Sándor Jancsó, Debrecen; Éva Medgyesi, née, Lukács, Debrecen; György Bacsa, Debrecen, all of Hungary

[73] Assignees: MTA Kozponti Kemial Kutato Intezete; BIOCAL Cyogyszergvar, both of Hungary

[21] Appl. No.: 352,420

[22] Filed: May 16, 1989

Related U.S. Application Data

[62] Division of Ser. No. 204,724, Jun. 10, 1988, Pat. No. 4,880,785.

[30] Foreign Application Priority Data

Aug. 7, 1987 [HU] Hungary .................. 2251-3596/87

[51] Int. Cl.$^5$ .................. A61K 31/70; C07H 19/073
[52] U.S. Cl. .................. 514/50; 536/22; 536/23
[58] Field of Search .................. 514/50; 536/23

[56] References Cited

PUBLICATIONS

Gauri et al., Chemotherapy, 18, pp. 269–273, 1973.
De Clercq et al., Current Chemotherapy, pp. 352–354, 1978.

Primary Examiner—Joseph L. Schofer
Assistant Examiner—Gary L. Kunz
Attorney, Agent, or Firm—Keil & Weinkauf

[57] ABSTRACT

A method of treating herpes eye infections with an ophthalmic composition comprising 5-propyl-2'-deoxyuridine.

1 Claim, 1 Drawing Sheet

METHOD OF TREATING HERPES EYE INFECTIONS WITH 5-PROPYL-2'DEOXYURIDINE

This is a division of application Ser. No. 204,724, filed June 10, 1989, now U.S. Pat. No. 4,880,785, now U.S. Pat. No. 4,880,785.

The invention relates to externally applicable, antiviral pharmaceutical compositions accumulating in the skin and a process for the preparation of same.

It is well known that the number of infections caused by herpes viruses is continuously increasing in spite of the extensive medical educational campaign and of the present results of chemotherapy. Therefore there is an ever increasing need for antiviral compositions for internal use, such as tablets, injections, infusion solutions, etc. (Saral, R. et al.: N. Eng. J. Med. 305, 63–67 /1981/). Compositions for external use are also applied in the therapy of herpes infections.

5-Substituted 2'-deoxyuridines comprising also halogen atoms in the substituent such as (E)-5-chlorovinyl-2'-deoxyuridine, (E)-5-bromovinyl-2'-deoxyuridine and (E)-5-iodovinyl-2'-deoxyuridine are very effective antiherpes virus compounds (De Clercq, E. and Walker, R. T.: Pharm. Therapy 26, 1 /1984/). From the 5-substituted 2'-deoxyuridines containing halogen atoms, 5-iodo-2'-β-deoxyuridine (IDU) has also been introduced into the medical practice as the active ingredient in a number of antiviral compositions for external use despite its low chemical stability and toxic decomposition products (Prusoff, W. H. and Goz, B.: in Sartorelli, A. C. and Jones, D. G.: Antineoplastic and Immunosuppressive Agents, Part II, pp. 272–347, Springer Verlag, New York, 1975).

Among the pyrimidine derivatives 5-alkyl substituted 2'-β-deoxyuridines have also been tested for antiviral activity. In in vitro conditions these compounds exerted much lower efficiency than the halo derivatives (De Clercq, E. et al.: Curr. Chemother, 352–354 /1978/).

E. De Clercq has carried out the in vitro tests of 5-substituted 2'-deoxyuridines against herpes simplex virus type 1 (Proc. of the 4th Int. Round Table on Nucleosides, Nucleotides and Their Biological Applications, Antwerpen, 1981). Fibroblast cell cultures freshly isolated from human embryo were infected with herpes virus HSV-1 (HIL as referred to in the literature). By changing the concentration of the infecting virus he determined the dose of virus causing cytopathogenic effect in 50% of the infected cell cultures [TCID$_{50}$ (tissue culture infective dose 50%)]. Cell cultures were infected with the test virus in a concentration corresponding to TCID$_{50}$, and solutions of each 5-substituted 2'-deoxyuridine derivative dissolved in the nutrient medium in different concentrations were added to the infected cell cultures. Nutrient medium: Minimal Essential Medium Eagle (MEM, GIBCO) with Earles Salts. This was supplemented with 10% of calve serum, 10 IU/ml of penicillin and 100 μg/ml of streptomycin in his experiments, at pH 7.4. By this method the minimum concentration of the active ingredient required to decrease the TCID$_{50}$-value of the virus by one logarithmic unit can be determined. Results obtained in this way and well characterizing the efficacy of the compounds are summarized in Table 1.

TABLE 1

| Compound tested | Minimum inhibitory concentration against HSV-1 (μg/ml) |
|---|---|
| 5-Bromovinyl-2'-deoxyuridine (BVDU) | 0.008 |
| 5-Ethyl-2'-deoxyuridine (EDU) | 0.5 |
| 5-Iodo-2'-deoxyuridine (IDU) | 0.13 |
| 5-Isopropyl-2'-deoxyuridine (IPDU) | 4 |

Data in Table 1 indicates that 5-isopropyl-2'-β-deoxyuridine of formula (I) (IPDU) exerts an antiherpetic activity lower by one order of magnitude than that of the other 5-substituted 2'-β-deoxyuridines, and is practically ineffective against herpes simplex viruses in vitro. This finding is in good agreement with the statement of K. K. Gauri and R. D. Walter (Chemotherapy 18, 269 /1973/) who concluded that 5-isopropyl-2'-β-deoxyuridine cannot be applied in the therapy of herpes virus.

It is the object of the present invention to provide a pharmaceutical composition for external use that can be applied more efficiently than the former compositions for dermatological treatment of the lesions caused by various herpes viruses.

The invention is based on the recognition that 5-isopropyl-2'-β-deoxyuridine applied onto the skin in an appropriate carrier accumulates in the skin and, in this way, it possesses excellent antiviral properties.

Table 2 summarizes the results of pharmaceutical examinations. Studies were carried out with $^{14}$C-labelled 5-isopropyl-2'-β-deoxyuridine. Results proved that an ointment composition containing IPDU applied on the skin is resorbed completely during 15 minutes and, contrary to expectations, 20–25% of the resorbed active ingredient accumulates in the skin and its concentration remains practically unchanged for about 8 hours.

The invention is further based on the recognition that the accumulation of the active agent in the skin proved to be very selective. This means that 75–80% of the dose resorbed enters the blood stream and the organs of the body wherefrom it is rapidly eliminated. In the organs listed in Table 3 concentration of IPDU diminishes below the detectable level within 3–6 hours.

TABLE 2

| Time (min.) | Total radioactivity resorbed | Radioactivity measured in the skin |
|---|---|---|
| | presented as percent of the radioactivity applied | |
| 15 | 27.9 | 9.25 |
| 30 | 30.5 | 6.60 |
| 60 | 32.9 | 7.70 |
| 120 | 30.8 | 6.00 |
| 180 | 26.0 | 7.25 |
| 240 | 20.7 | 5.90 |
| 480 | 26.7 | 5.40 |

TABLE 3

| Time (hours) | Relative radioactivity $\frac{dpm/mg\ organ}{dpm/mg\ skin}$ | | | | | |
|---|---|---|---|---|---|---|
| | skin | brain | kidney | liver | spleen | lung |
| 0.25 | 1.00 | 0.0006 | 0.01 | 0.008 | 0.005 | 0.008 |
| 0.50 | 1.00 | 0.0004 | 0.005 | 0.010 | 0.005 | 0.008 |
| 3.00 | 1.00 | 0.0001 | 0.003 | 0.002 | 0.002 | 0.002 |
| 6.00 | 1.00 | 0.0001 | 0.001 | 0.002 | 0.002 | 0.002 |

Data in Table 3 clearly indicate that the radioactive agent accumulates predominantly in the skin among the organs listed, that is, resorption of IPDU into the skin tissue is selective.

Finally the invention is based on the recognition that IPDU, contrary to the other pyrimidine nucleosides known for medical application, is remarkably stable against degrading enzymes that cleave nucleosides to base and 2-deoxyribose-1-phosphate. This was proved both by enzymatic reactions (see FIG. 1) and in vivo metabolism experiments performed with $^{14}$C-labelled IPDU.

In FIG. 1 the rate of cleavage of thymidine, 5-ethyl-2'-β-deoxyuridine (EDU) and 5-isopropyl-2'-β-deoxyuridine (IPDU) by thymidine phosphorylase enzyme is shown.

Figure 2:
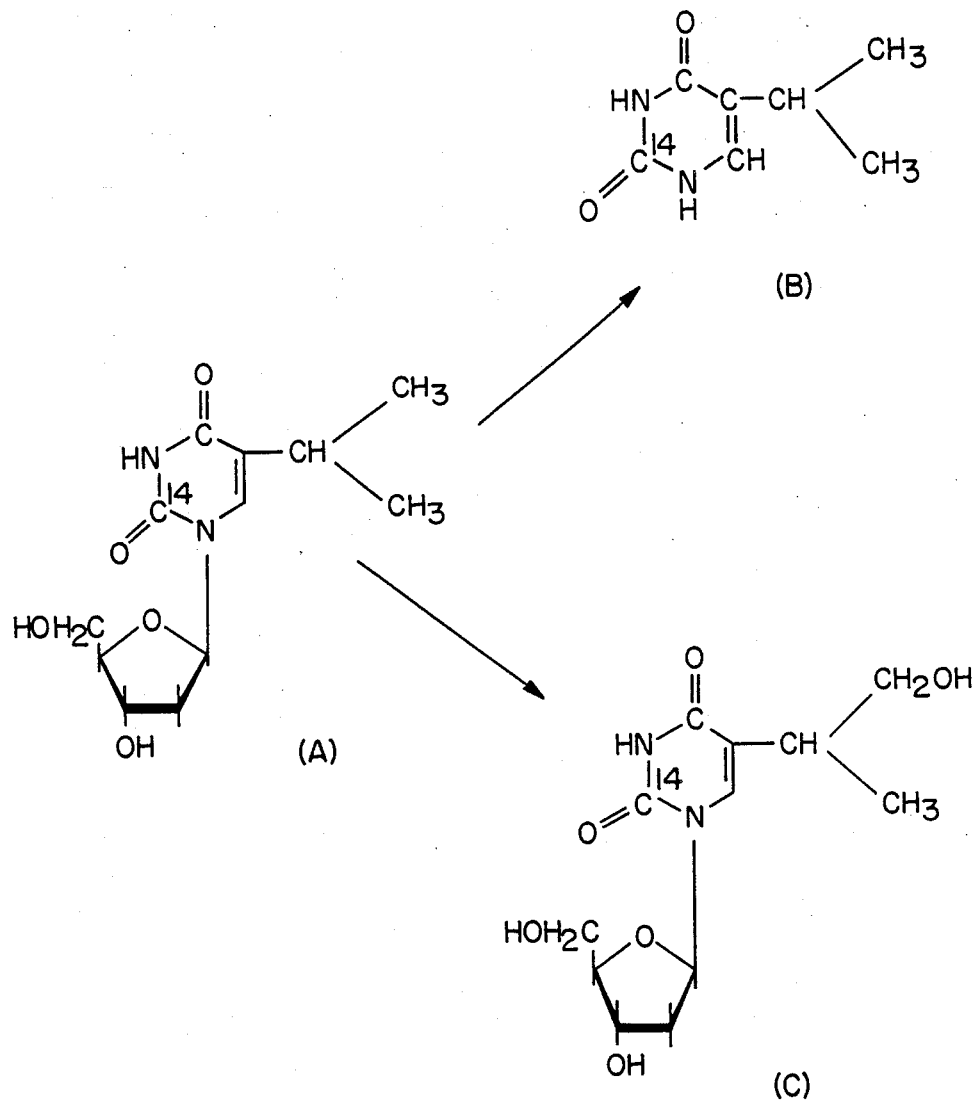

FIG. 2 shows the metabolytic products identified in the urine of mice treated with IPDU (I) (i.p. 200 mg/kg). This figure proves that 80–85% of IPDU (I) is eliminated from the body in unchanged form, whereas only 2 to 5% are eliminated in the form of 5-isopropyluracil and 10 to 15% in the form of 5-(1-methyl-2-hydroxyethyl)-2'-deoxyuridine.

In our experiments it has also been determined that 5-isopropyl-2'-β-deoxyuridine is practically non-toxic, it exerts no mutagenic or teratogenic effect and it does not provoke skin lesion or allergy even when applied in the multiple of the therapeutically effective dose. On the basis of these favourable properties 5-isopropyl-2'-β-deoxyuridine can be excellently used as an active ingredient of antiviral, first of all antiherpes virus, composition for dermatological use.

Based on the above recognitions the invention relates to pharmaceutical antiviral compositions for external use, accumulating in the skin. This composition comprises 0.02–5% by mass of 5-isopropyl-2'-β-deoxyuridine together with carriers, diluents and/or other additives conventionally used in the production of pharmaceutical compositions for external use.

The antiviral composition of the invention can be prepared by mixing 0.02–5% by mass of 5-isopropyl-2'-β-deoxyuridine with carriers, diluents and/or other additives conventionally used in the production of pharmaceutical compositions for external use.

The pharmaceutical antiviral composition according to the invention comprises for ophthalmological purposes 0.1–1% by mass of 5-isopropyl-2'-β-deoxyuridine with carriers, diluents and/or other additives conventionally used in the production of pharmaceutical compositions.

The pharmaceutical compositions according to the invention exert remarkable antiviral efficiency. They can be prepared in the form of ointment, gel, emulsion, suspension, solution, spray, adhesive, etc. The content of the active ingredient in the antiviral compositions varies according to the mode of application and treatment. Satisfactory results can generally be obtained by applying 0.3–2% by weight of 5-isopropyl-2'-β-deoxyuridine onto the skin to be treated.

For the preparation of the pharmaceutical compositions according to the invention lanoline, vaseline, polyethylene glycol, waxes, furthermore water and organic solvents such as ethanol can be used in the first place. Depending on type of the composition stabilizers, emulsifying, surface active and colouring agents and other additives can also be applied.

The pharmaceutical composition according to the invention may also contain, in addition to 5-isopropyl-2'-β-deoxyuridine, other biologically active substances, for example antiphlogistic agents such as chloramphenicol, skin-tranquillizers such as azulene, skin siccative agents such as zinc oxide, etc.

The pharmaceutical compositions according to the invention can be prepared by generally known pharmacotechnological procedures.

5-isopropyl-2'-β-deoxyuridine is a known compound and can be prepared by procedures described in the literature, for example: Szabolcs, A., Sági, J. and Ötvös, L.: Carbohydrates, Nucleosides and Nucleotides 2, 197–211 (1975); Nucleic Acids Res. 1, 49–52 (1975). The physical characteristics of the compound are as follows: it is a white, crystalline, unscented powder with a slightly bitter flavour. Melting temperature: 181°–183° C. The compound is soluble in water, methanol and ethanol, the solubilities being at room temperature 7.9 mg/cm$^3$, 25.4 mg/cm$^3$ and 11 mg/cm$^3$, respectively. It is practically insoluble in benzene, chloroform and diethylether. It can be stored for years at room temperature without decomposition.

Thin layer chromatography of the compound on silica gel sheet (Merck) with ethylacetate-methanol (95:5) provided an $R_f$-value of 0.43. Ultraviolet absorption maximum was found to be at 267.4±0.4 nm with a molar extinction coefficient of 9500±400; n=50).

Toxicological and skin innocuity examinations

Acute toxicity

Acute toxicity values were determined on mice, rats and rabbits. The compound was administered to the animals intraperitoneally over 14 days, and the following LD$_{50}$-values were observed:
Mice: 920 mg/kg
Rats: 820 mg/kg
Rabbits: 2000 mg/kg 30-day toxicity on rats The animals were given a daily dose of 5–50 mg/kg of the active agent intraperitoneally over 30 days. During the test period no difference was observed between treated and untreated (control) animals. No differences in weight increase, food intake, nor lesions in the nervous system and death were observed. Autopsy results did not refer to any effect related to toxic alterations.

6-week acute and subacute toxicology tests on rabbits

Animals were treated intraperitoneally with a daily dose of 3–30 mg/kg of the active ingredient. No toxic symptoms, alterations in body weight and no deaths were observed either during the 6-week treatment period or during an additional 2-week observation period. No histological lesions were found by dissection.

Mutagenic and carcinogenic effect of the active agent as determined by Ames test Examinations were carried out by using mutants of Salmonella typhimurium bacteria. Aqueous suspension or solution of 0.0125–8.0% by weight of 5-isopropyl-2'-β-deoxyuridine, furthermore solid powdered form of the active agent were applied in the experiments. Diffusion-reversion test, liquid-reversion test (Ames, B. N. et al.: Proc. Natl. Acad. Sci. USA 71, 2281 /1973/), and other tests with S9 fractions (Ames, B. N. et al.: Mutat. Res. 31, 347 /1975/) were used in the studies. Neither mutagenic nor carcinogenic effects were observed.

Examination of mutagenicity, teratogenicity and embryo-toxicity under in vivo conditions These examinations were carried out by using Roussel's "Mouse Spot Test" (Roussel, L. B. and Majos, M. H.: Genetics 42, 161-175 /157/, Roussel, L. B et al.: Mutation Res. 86, 355-359 /1981/) on C57/BL mice. Physiological saline solution of 5-isopropyl-2'-β-deoxyuridine was applied in 460 and 230 mg/kg concentration, respectively. In case of the dose of 230 mg/kg which is 45 times higher than the therapeutical dose neither mutagenic and embriotoxic nor teratogenic effect was observed.

Resorption test

Examinations were carried out on white male CFLP mice of 23-25 g body weight with the use of an ointment, prepared according to Example 1, containing 0.8% by weight of $^{14}$-C-labelled 5-isopropyl-2'-β-deoxyuridine. The ointment was used in a dose of 50 mg/animal. 5—5 animals were utilized for each experiment. The abdominal skin of the animals was depilated with "Depilan" (registered trademark, Hamol International, Krk, Yugoslavia). 24 hours after depilation the animals were fixed dorsally and the ointment was applied on a 2 cm$^2$ region of the depilated skin. Fastened animals were held in metabolism chamber for 8 hours, then the treated skin surface was wiped and the animals were allowed to move freely until the end of the observation period. Observation times were 15, 30, 60, 120, 180, 360 and 480 minutes. Radioactivity of the wiped material and that accumulated in different organs of the treated animals (skin, blood, liver, spleen, kidney, lung and brain) was determined together with radioactivity in urine of the animals collected throughout 24 hours. The data are shown in Table 4.

from the different organs. Data show that radioactive material can be detected only in trace amounts 3 hours after the treatment (Table 3).

On the other hand, the radioactive material is well accumulated into the skin and its concentration remains approximately unchanged for 8 hours, as it is clearly indicated by the data in Table 2.

Tolerance test

Investigations were carried out with white mice of 25-30 g body weight. The skin of the test mice was healthy or scarified. 2-3 cm$^2$ of the skin area of the test mice were treated daily with an ointment containing 2.5% by mass of 5-isopropyl-2'-β-deoxyuridine for 6 weeks. The control group of mice was treated with an ointment containing no active agent (placebo).

After the treatment period animals were kept under observation for 2 weeks. No alterations (skin irritation, allergic phenomena or inflammation) were detected on treated mice either during the treatment period or the observation period. No histopathological changes could be detected, either.

Clinical tests

Clinical experiments were performed on volunteers with diagnosed herpes simplex, herpes genitalis and herpes zoster virus infection, respectively. Depending on the disease the patients were treated 3-5 times daily for 5-10 days with the pharmaceutical composition according to the invention. Clinical tests were carried out by double blind method. The effectivity of the composition of Example 1(A) was examined in comparison with the commercially available ointment 5-iodo-2'-β-deoxyuridine (C) and the placebo ointment which did not contain active agent (B). Results of the clinical tests are summarized in Table 5.

TABLE 5

| Effect | Herpes simplex | | | Herpes genitalis | | | Herpes zoster | | |
|---|---|---|---|---|---|---|---|---|---|
| | "A" | "B" | "C" | "A" | "B" | "C" | "A" | "B" | "C" |
| Excellent | 31 | 6 | 14 | 11 | 0 | 10 | 16 | 0 | 3 |
| Appropriate | 9 | 10 | 13 | 7 | 2 | 6 | 7 | 2 | 1 |
| Moderate | 9 | 10 | 9 | 3 | 5 | 5 | 3 | 5 | 3 |
| Ineffective | 1 | 24 | 14 | 0 | 13 | 1 | 0 | 1 | 3 |
| Deterioration | 1 | 1 | 1 | 1 | 1 | 0 | 0 | 0 | 0 |
| Number of patient | 51 | 51 | 51 | 22 | 21 | 22 | 26 | 8 | 10 |

"A" Ointment containing 5-isopropyl-2'-β-deoxyuridine
"B" Placebo ointment
"C" Ointment containing 5-iodo-2'-β-deoxyuridine (control)

TABLE 4

| Time (min.) | Radioactivity wiped (%) | Radioactivity resorbed (%) |
|---|---|---|
| 0 | 100 | 0 |
| 15 | 72.1 | 27.9 |
| 60 | 67.1 | 32.9 |
| 120 | 68.2 | 30.8 |
| 180 | 74.0 | 26.0 |
| 240 | 79.3 | 20.7 |
| 480 | 73.3 | 26.7 |

According to the data in Table 4 radioactivity of the resorbed material practically did not change after the first 15 minutes, that is the radioactive material is resorbed into the skin from the ointment composition during 15 minutes and remains in the skin for a very long period of time. The sum of the radio-activity measured in the skin, blood and other organs indicates that 20-35% of the active agent is resorbed from the ointment, and 65-80% of this amount are rapidly eliminated The main advantages of the composition and process according to the invention are as follows:

(a) The active agent of the composition is rapidly and selectively resorbed into the skin where it is accumulated and, in this way, the desired effect can be attained by the use of the composition with a low active ingredient content.

(b) As a consequence of topical application of the composition, the amount of the active agent to be used is less than in case of using a composition for internal application.

(c) The active ingredient of the composition is remarkably stable. This stability also contributes to the favourable results obtained with compositions of low active ingredient content.

The composition and process according to the invention are elucidated in detail by the following non-limiting examples.

| Example 1 | |
|---|---|
| Ointment for dermatological use | |
| 5-Isopropyl-2'-β-deoxyuridine | 8 g |
| Polysorbate 60 (Ph. Hg. VII. 731) | 36 g |
| Liquid paraffin | 50 g |
| Cetyl-stearyl alcohol (Ph. Hg. VII. 731) | 80 g |
| White vaseline | 100 g |
| Glycerol | 200 g |
| White wax | 4 g |
| p-Hydroxybenzoic acid methylester | 2 g |
| Distilled water | 500 g |

The ointment can be stored without decomposition for at least 2 years at room temperature.

| Example 2 | |
|---|---|
| Gel for dermatological application | |
| 5-Isopropyl-2'-β-deoxyuridine | 1.0 g |
| Methyl cellulose | 4.0 g |
| Glycerol | 20.0 g |
| Distilled water | 73.9 g |
| Sodium benzoate | 0.1 g |

| Example 2 | |
|---|---|
| Gel for dermatological application | |
| Ethanol (96%) | 0.9 g |
| p-Hydroxy-benzoic acid ethylester (nipagin) | 0.1 g |

| Example 3 | |
|---|---|
| Ointment for ophthalmological application | |
| 5-Isopropyl-2'-β-deoxyuridine | 0.8 g |
| Occulentum simplex | 999.2 g |
| The composition of the occuléntum simplex is as follows: | |
| Lanae alcoholes (wool wax alcohols) (Ph Hg VII, 1088) | 50 g |
| Paraffinum liquidum (liquid paraffine) (Ph Hg VII, 1283) | 250 g |
| Vaselinum album ophthalmicum (white vaseline) | 700 g |

We claim:
1. The process of treating a herpes infection in the eye by the application of an opthalmic composition to the eye, which composition comprises 0.02–5% by mass of 5-isopropyl-2'-B-deoxyuridine admixed with carriers, diluents and/or other additives conventionally used in the production of pharmaceutical compositions for opthalmic use.

* * * * *